(12) United States Patent
Ayrenschmalz

(10) Patent No.: US 7,893,956 B2
(45) Date of Patent: Feb. 22, 2011

(54) IMAGE PICK-UP MODULE AND METHOD FOR ASSEMBLY OF AN IMAGE PICK-UP MODULE

(75) Inventor: Robert Ayrenschmalz, Niederaichbach (DE)

(73) Assignee: Karl Storz GmbH & Co. KG (DE)

( * ) Notice: Subject to any disclaimer, the term of this patent is extended or adjusted under 35 U.S.C. 154(b) by 1479 days.

(21) Appl. No.: 11/286,046

(22) Filed: Nov. 23, 2005

(65) Prior Publication Data

US 2006/0109368 A1    May 25, 2006

(30) Foreign Application Priority Data

Nov. 23, 2004   (DE)  ................ 10 2004 056 946

(51) Int. Cl.
*A61B 1/00* (2006.01)
*A62B 1/04* (2006.01)
*H04N 9/47* (2006.01)

(52) U.S. Cl. ................................. 348/65; 600/106
(58) Field of Classification Search ............ 348/65, 348/75, 76; 600/106, 117
See application file for complete search history.

(56) References Cited

U.S. PATENT DOCUMENTS

| 4,745,470 A | 5/1988 | Yabe et al. ............ 358/98 |
| 4,745,471 A | 5/1988 | Takamura et al. |
| 4,831,456 A | 5/1989 | Takamura ............ 358/229 |

(Continued)

FOREIGN PATENT DOCUMENTS

DE    37 36 688    6/1988

(Continued)

OTHER PUBLICATIONS

European Search Report; Feb. 21, 2006; 4 pages.

(Continued)

*Primary Examiner*—Gims S Philippe
(74) *Attorney, Agent, or Firm*—St. Onge Steward Johnston & Reens LLC

(57) ABSTRACT

The invention relates to an image pick-up module, in particular for an endoscope, comprising an electronic image sensor having a plurality of contact fingers that are arranged in two rows on opposite sides and each have a length, and a circuit board, to which the contact fingers are electrically contact-connected, the circuit board having at least three sections which are connected to one another in one piece and of which a first and a second section extend in a manner spaced apart from one another essentially transversely with respect to the image sensor and a third section extends essentially parallel to the image sensor, the image sensor being arranged at the end of the first and second sections which is remote from the third section, and at least one row of the contact fingers of the image sensor running along an outer side of the first or second section. The first section, the second section and the third section are connected to one another in an unarticulated manner, the length of the first section and/or of the second section is less than or equal to the length of the contact fingers and a space is present between the first, second and third sections of the circuit board, at least one electronic component for the control electronics of the image sensor being present in the said space.

26 Claims, 9 Drawing Sheets

U.S. PATENT DOCUMENTS

| | | | |
|---|---|---|---|
| 5,220,198 A | 6/1993 | Tsuji | |
| 5,402,768 A * | 4/1995 | Adair | 600/106 |
| 5,754,313 A | 5/1998 | Pelchy et al. | 358/473 |
| 5,857,963 A | 1/1999 | Pelchy et al. | 600/109 |
| 6,142,930 A | 11/2000 | Ito et al. | 600/109 |
| 2002/0080233 A1* | 6/2002 | Irion et al. | 348/65 |
| 2002/0142510 A1 | 10/2002 | Adachi | 438/57 |
| 2004/0167378 A1 | 8/2004 | Ando | |
| 2004/0263680 A1 | 12/2004 | Sonnenschein et al. | |
| 2005/0119527 A1* | 6/2005 | Banik et al. | 600/117 |

FOREIGN PATENT DOCUMENTS

| | | |
|---|---|---|
| DE | 199 24 189 A1 | 1/2001 |
| JP | 05115436 A | 5/1993 |
| JP | 2000209472 A | 7/2000 |
| JP | 2001104247 | 4/2001 |
| JP | 2001245186 A | 9/2001 |
| JP | 2002034910 A | 2/2002 |

OTHER PUBLICATIONS

Japanese Office Action; Patent Application No. JP 2005-333043; Dispatched Apr. 1, 2008; 3 pages. Translation.

* cited by examiner

IMAGE PICK-UP MODULE AND METHOD FOR ASSEMBLY OF AN IMAGE PICK-UP MODULE

CROSS REFERENCE TO RELATED APPLICATION

The present application claims priority of German patent application 10 2004 056 946.0 filed on Nov. 23, 2004.

BACKGROUND OF THE INVENTION

The invention relates to an image pick-up module, in particular for an endoscope or a miniature camera, comprising an electronic image sensor having a plurality of contact fingers that are arranged in two rows on opposite sides, and a circuit board, to which the contact fingers are electrically contact-connected.

The invention furthermore relates to a method for assembly of an image pick-up module.

An electronic image pick-up module is generally used in video recording technology. Besides the use in video cameras, such electronic image pick-up modules are used, in as miniaturized a design as possible, in particular also in endoscopes for technical or medical purposes. Such an endoscope or video endoscope is disclosed for example in U.S. Pat. No. 5,754,313.

An image pick-up module generally comprises an electronic image sensor or image pick-up that converts light incident on it into an electrical signal. Generally, such electronic image sensors are embodied using CCD or CMOS technology.

Thus, miniaturized image sensors that are produced using TAB (tape automated bonding) technology are preferred at the present time. Image sensors of this type have contact fingers that are arranged in two rows on opposite sides of the image sensor and are contact-connected to the circuit board of the image pick-up module.

The circuit board of the image pick-up module serves not only for contact-connecting the image sensor, but also, as in the case of the image pick-up module disclosed in DE-A-199 24 189, for receiving electronic components, such as transistors or capacitors, which constitute parts of the control electronics of the image sensor.

In the case of the known image pick-up module just mentioned, the circuit board is formed from a one-part plate that can be folded along flexible connecting sections and can be folded to form a parallelepipedal body that is essentially U-shaped in cross section. In the folded state, the circuit board body has two sections that extend essentially transversely with respect to the image sensor and are spaced apart from one another and a third section running essentially parallel to the image sensor, the image sensor being fitted to that end of the first and second sections of the circuit board body which is at a distance from the third section. The third section of this circuit board of the known image pick-up module serves for the leadthrough of an electrical cable leading away from the circuit board, and in particular for the strain relief for this cable. By contrast, electronic components for the control electronics of the image sensor are fitted on the inner side of a fourth section of the circuit board, from the outer side of which the image sensor is arranged.

The use of such image pick-up modules in endoscopes has only become possible due to the miniaturization of the image sensors and the advances in microtechnology. In an endoscope, the image pick-up module is usually arranged in the distal tip, that is to say the tip facing the patient, of the endoscope shaft, as is described for example in U.S. Pat. No. 5,754,313. In this case, the image pick-up module replaces the image transmission optical system that is provided in "traditional" endoscopes and is formed from a serial arrangement of lenses. Instead of transmitting the image received at the distal end to the proximal end, that is to say to the end remote from the patient, by means of an optically imaging lens system, in an image pick-up module the optical light signals are converted into electrical signals and transmitted to the proximal end to the camera control unit via at least one cable or generally a cable system.

In endoscopes, the outer contour of the shaft is always required to have the smallest possible cross section. Accordingly, the image pick-up modules used have to have the smallest possible external cross section in order to find space in such a shaft. By way of example, in the case of a video endoscope for medical purposes, the shaft diameter is only a few mm, in any event less than 10 mm. This means that the dimensions of the miniaturized image pick-up module should be embodied as small as feasibly possible, i.e. as far as possible less than 6 mm. A compact design of an image pick-up module is therefore desirable.

On the other hand, the image pick-up module of integrated design should contain a series of components (e.g. amplifier) required for the function of the image sensor, so that the image pick-up module only also has to be connected to a customary multi-core cable which, in the case of using the image pick-up module in an endoscope in the distal tip thereof, produces the voltage supply and signal transmission between the image pick-up module and a control circuit (camera control unit) at the proximal end of the endoscope or in an external device.

The image pick-up module disclosed in U.S. Pat. No. 5,754,313 has two separate circuit boards, that is to say not a single circuit board in one piece for contact-connecting the image sensor, the two circuit boards, in a customary manner, receiving miniature electronic components and serving for contact-connecting the cable or cable system that leads away. In this case, the two circuit boards run parallel to one another and approximately at right-angles to the area of the image sensor. Since the signal electronics cannot function independently on the two circuit boards, an electrical connection, for example in the form of lines or a connecting circuit board, additionally has to be integrated, thereby increasing the mounting outlay of this known image pick-up module. The space between the two separate circuit boards is filled with a curing plastic. In this case, the cable moving away from the circuit board is contact-connected to the two circuit boards on the outer side thereof, and the contact fingers of the image sensor are likewise contact-connected to the circuit boards on the outer side of the two circuit boards at the distal end of the contact-making points of the cable leading away.

Consequently, this known image pick-up module also has a length in the transverse direction with respect to the image sensor which significantly exceeds the side dimensions of the image sensor.

A further requirement made of an image pick-up module of this type is that the image pick-up module should be able to be produced cost-effectively and with little time being spent; in particular, the assembly of the individual components of the image pick-up module should be able to be carried out as simply as possible despite the miniaturization and compactness of the image pick-up module.

U.S. Pat. No. 4,745,471 describes a further image pick-up module, in the case of which the image sensor is arranged on a one-piece circuit board that is U-shaped in cross section. In this case, the image sensor is embedded in the U-shaped groove of the circuit board, as a result of which, although a very short structural length in the direction transversely with respect to the image sensor is achieved, electronic components nevertheless then have to be fitted and contact-connected on the outer side of the circuit board in the case of this known image pick-up module, as a result of which these components have little protection against external influences.

SUMMARY OF THE INVENTION

It is an object of the invention to develop an image pick-up module to the effect that it has a compact construction overall, in particular has a structural length that is as short as possible in the direction transversely with respect to the image sensor, and that the image pick-up module can be produced easily.

The invention is furthermore based on the object of specifying a method for assembly of an image pick-up module which can be carried out in a simple manner.

According to an aspect of the invention, an image pick-up module is provided, comprising an electronic image sensor having a body and a plurality of contact fingers arranged in two rows on opposite sides of the body and each having a length; a circuit board to which the contact fingers are electrically contact-connected, the circuit board having at least three sections connected to one another in one piece, a first and a second section of the at least three sections extending in a manner spaced apart from one another essentially transverse with respect to the image sensor, and a third section of the at least three sections extending essentially parallel to the image sensor; the first, second and third sections being connected to one another in an unarticulated manner, the image sensor being arranged at an end of the first and second sections which is remote from the third section, at least one of the two rows of the contact fingers of the image sensor running along an outer side of at least one of the first and second sections; a length of at least one of the first and second sections being not larger than the length of at least a portion of the contact fingers; and at least one electronic component of control electronics for the image sensor, the at least one electronic component being arranged in a space present between the first, second and third sections of the circuit board.

The circuit board of the image pick-up module according to the invention is thus formed by a one-piece solid body having a notch or a groove, by virtue of the arrangement of at least one electronic component, preferably a plurality of electronic components, for the distal control electronics of the image sensor, for example a transistor (amplifier) and a capacitor. The image sensor is fitted on the "open" side of the circuit board or the U-shaped cross section, for example is adhesively bonded onto the free ends of the first section and of the second section of the circuit board. In this way, the image pick-up module may be formed with an overall parallelepipedal or preferably cuboid external contour, the edge length of which corresponds to the edge length of the image sensor in the plane thereof. The unarticulated or rigid connection of the three sections to one another creates an overall very stable design of the image pick-up module, the rigid circuit board simultaneously serving as a housing and thus affording protection for the components situated therein. Furthermore, the length of the circuit board in the direction transversely with respect to the image sensor is chosen to be small enough that it is not greater than the length of the contact fingers of the image sensor, which has the further advantage that the contact fingers running along at least one outer side of the first or second section can even be contact-connected to the circuit board on the outer side or underside of the third section, as is provided in one preferred refinement.

In one preferred refinement, the contact fingers of the image sensor that run along the first or second section at least partly engage on an outer side of the third section of the circuit board and are contact-connected to the circuit board at the said outer side.

The advantage of this measure is that, in conjunction with the fixed configuration of the circuit board, the contact fingers engaging around the outer side of the third section on the one hand further increase the overall stability of the image pick-up module, but on the other hand also ensure the fastening of the image pick-up module to the circuit board. In this case, it may be provided that only individual ones of the total number of contact fingers engage around the outer side of the third section of the circuit board, while the rest of the contact fingers end at the outer side of the first and/or second section. The contact-connection of at least a portion of the contact fingers or preferably of all the contact fingers of the image sensor at the outer side of the third section, as is provided in a further preferred refinement, has the advantage that the cross-sectional dimensioning of the outer contour of the image pick-up module is not increased by lateral contact-connecting locations, rather that the outer sides of the first and second sections may terminate essentially flush with the corresponding side edges of the image sensor.

For this purpose, it is furthermore preferred for depressions for receiving the contact fingers to be formed on the outer side of the first and/or second section.

This measure furthermore contributes to the fact that the cross-sectional dimensions of the image pick-up module, in conjunction with a maximum usable cross-sectional dimensioning of the circuit board that corresponds to the cross-sectional dimensioning of the image sensor, the contact fingers do not lead to a further increase in cross section since they are embedded in the depressions on the outer sides of the first and/or second section.

In a further preferred refinement at least two electronic components are arranged in the space in a manner lying one above the other in the direction from the third section to the image sensor.

In the case of this measure, the space, that is to say the abovementioned groove or notch in the circuit board, in conjunction with a compact design of the module, is optimally utilized for receiving electronic components. In this case, the electronic components, proceeding from the third section on which a transistor is fixed, by way of example, are arranged one atop the other in a stacked arrangement and fixed to one another. Consequently, the internal space of the circuit board is utilized three-dimensionally, which enables the dimensions of the outer contour of the circuit board to be reduced.

In a further preferred refinement, the at least one electronic component is contact-connected to at least one conductor wire at a location of the space which is at a distance from the first, second and third sections.

In the case of this measure, by way of example, if the electronic component is a transistor that usually has three contact fingers, each individual contact finger is connected to the circuit board by means of a conductor wire. Fitting the conductor wire to the respective contact finger at a location of the space or the groove or the notch which is at a distance from the first, second and third sections has the advantage that the space between the three sections, as mentioned previously, is optimally utilized in terms of its three-dimensional extent, which contributes to the fact that the three sections of the circuit board can themselves be kept small with regard to their two-dimensional dimensions.

In this case, it is furthermore preferred for the at least one conductor wire, proceeding from the at least one electronic component, to be at least partly led through a hole that extends through the first or second section and opens at the outer side of the third section.

In this case, it is advantageous that the required contact-connection of the at least one electronic component arranged in the internal space of the circuit board is also effected on the outer side of the circuit board, in particular on the outer side of the third section, which makes the contact-connection, for example by means of a soldering connection, particularly simple because the outer side of the third section is easily accessible. The leadthrough of the conductor wire through a hole through the first, second or third section has the advantage that the through-plating onto the outer side of the third section is effected through the material of the circuit board and, consequently, does not require any additional space. This measure is also advantageous from insulation standpoints, particularly if the circuit board is produced in its entirety from an insulating material, for example from a hard plastic, since it is then possible to provide a plurality of such holes which are spaced apart from one another, so that each conductor wire can be led through a dedicated hole to the outer side of the third section in a manner insulated from the other conductor wires. The holes may be at least partly metallized, so that the conductor wires do not have to be led completely through the holes, rather the electrical conduction is effected via the metallization of the holes to the outer side of the third section.

In a further preferred refinement, the remaining free part of the space between the first, second and third section and the at least one electronic component is filled with an insulating curable filling composition.

The curable filling composition has the advantage, on the one hand, that after curing it further stabilizes or reinforces the entire arrangement comprising image sensor, circuit board and the at least one electronic component, and, on the other hand, it also advantageously serves to insulate the conductor wires that are present for contact-connecting the component or the components.

In a further preferred refinement, the circuit board is produced from a parallelepipedal, in particular approximately cuboid, bulk material, and in that the space between the first, second and third sections is formed by a material cutout from the bulk material.

This measure has the advantage, on the one hand, that the circuit board can be produced easily by means of the material cutout in an operation that can be carried out particularly simply and, on the other hand, the finished circuit board also has the desired high stability since it is formed from a bulk material as starting material.

In a further preferred refinement the space between the first, second and third sections has approximately the form of a T in cross section, the wider section of the space being situated at the ends of the first and second sections which face the image sensor.

The T-shaped configuration of the space between the three sections results in a step on the inner side of the first and second sections, which facilitates the leadthrough of conductor wires through the material of the first and second sections for contact-connecting components situated in the space between the three sections. Furthermore, the risk of the conductor wire undesirably acquiring contact with the image sensor is also avoided since the latter is spaced apart from the step in the first and second sections, while the conductor wires are positioned at the level of the step.

In a further preferred refinement, the image sensor is fixed directly to the ends of the first and second sections of the circuit board.

This measure does not lead to a reduced structural length of the image pick-up module, but rather contributes advantageously to the stabilization of the entire image pick-up module and simplifies the mechanical connection of the image sensor to the circuit board.

As already mentioned previously, it is further preferred for a plurality of holes or conductors to extend through the material of at least one of the first and second sections of the circuit board, proceeding from the outer side of the third, section, and to open or end at an inner side of the third section, of the first and/or second section.

The holes or conductors extending through the material of the three sections have the advantage of easy through-plating from the internal space of the circuit board to the outer side of the third section. This configuration is advantageous in particular with the abovementioned T-shaped configuration of the space between the three sections, the holes in the first and/or second section then advantageously opening in the step in the first and/or second section which is formed by the T-structure of the space.

For the purpose of a miniaturized configuration of the image pick-up module according to the invention, particularly if it is provided for use in an endoscope, it is provided that the image pick-up module is formed in approximately cuboid fashion and has side dimensions of approximately 2 mm×2 mm or smaller.

In a further preferred refinement, the circuit board is connected to a multi-core cable, the cable being contact-connected to the circuit board at the outer side of the third section.

In this case, it is advantageous that the contact-connection of the cable leading away from the circuit board to the circuit board can be realized particularly simply since the outer side of the third section is accessible particularly well for the contact-connecting operation. In this case, it is furthermore preferred for the cable to be releasably connected to the circuit board.

The releasable connection of the cable to the circuit board has the advantage that the image pick-up module can easily be disconnected from the cable for maintenance purposes and, by way of example, can thus also be easily dismantled from an endoscope. The releasable connection may be realized for example by the cable being contact-connected to a further circuit board that is complementary to the outer side of the third section of the circuit board. The cable is then fixedly connected to this additional circuit board, and the additional circuit board is then contact-connected to the outer side of the third section simply by being in contact and is connected for example by means of a conductive adhesive or by means of a readily releasable soldered joint.

In a further preferred refinement of the image pick-up module, a row of the contact fingers of the image sensor is cut to length and contact-connected to the circuit board on an outer side of the first or second section.

In this case, it is advantageous that more area for contact-connecting the cable system that leads away is available on the outer side of the third section of the circuit board.

In a further preferred refinement the first and/or the second section run obliquely with respect to the centre axis of the third section at least on the outer side towards the third section.

On account of this measure, the image pick-up module tapers on the outer side from the image sensor towards the proximal end, which is advantageous particularly with the abovementioned configuration if at least one row of the contact fingers of the image sensor is contact-connected to the circuit board not at the outer side of the third section but rather on the outer side of the first and/or second section, since then the cross-sectional dimensioning of the image pick-up module is not enlarged despite the contact fingers being contact-connected at the outer side of the first and/or second section.

According to another aspect of the invention, a method for assembly of an image pick-up module is provided, comprising providing an electronic image sensor having a body and a plurality of contact fingers arranged in two rows on opposite sides of the body and each having a length, providing a circuit board having at least three sections, a first and a second section of the at least three sections extending in a manner spaced apart from one another essentially in a first direction, and a third section of the at least three sections extending in a second direction essentially transversely with respect to the first direction, wherein the circuit board is provided with a length which is not larger than the length of the contact fingers and providing the circuit board with a space between the first, second and third sections, fitting the imagine sensor to an end of the first and second sections which is remote from the third section, arranging the contact fingers of at least one of the two rows along an outer side of at least one of the first and second sections and electrically contact-connecting the contact fingers to the circuit board, and inserting at least one electronic component in the space and contact-connecting the electronic component to the circuit board before fitting the image sensor to the circuit board.

In this case, it is preferred and advantageous for the purpose of a stable embodiment of the one-piece circuit board if the circuit board prior to its provision, is produced from a parallelepipedal, in particular approximately cuboid, bulk material, a groove being introduced into the bulk material by means of a material cutout, thereby forming the first, second and third sections of the circuit board and the space between these sections.

In the case where the control electronics for the image sensor comprise more than one electronic component, it is furthermore preferred if, before the image sensor is fitted, these electronic components are inserted into the space between the first, second and third sections and they are contact-connected to the circuit board, the at least two electronic components being fitted on the third section, i.e. on the inner side, in an arrangement lying one above the other.

In this case, by way of example, the first electronic component may be adhesively bonded onto the inner side of the third section, and the second electronic component is then adhesively bonded onto the first component, etc.

In a further preferred refinement, the at least one electronic component is contact-connected to at least one conductor wire at a location of the space between the first, second and third sections, the conductor wire then subsequently being contact-connected to the outer side of the third section.

The free space between the first, second and third sections which remains after the insertion of the at least one electronic component together with the at least one conductor wire is filled with a curing filling composition.

Since the free space embodied in the form of a groove or indentation, is open preferably on two sides running transversely with respect to the first and second sections, these sides are lined, for example with a film, before the filling composition is filled in, which film can easily be stripped from the filling composition preferably after the latter has cured.

In this case, it is furthermore preferred for the filling composition to be filled into the space between the three sections before the image sensor is fitted to the circuit board.

In this case, it is advantageous that the side of the circuit board to which the image sensor is later fitted can be utilized as a filling-in opening for filling in the filling composition.

In a further preferred refinement, at least the contact fingers of one row of the image sensor are diverted onto the outer side of the third section and are contact-connected to the circuit board on the said outer side.

Finally, preferably a multi-core cable is contact-connected to the circuit board at the outer side of the third section, this contact-connection preferably being releasable, as has already been described above.

Further advantages and features emerge from the description below and the accompanying drawing.

It goes without saying that the features mentioned above and the features still to be explained below can be used not only in the combination respectively specified but also in other combinations or by themselves, without departing from the scope of the present invention.

BRIEF DESCRIPTION OF THE DRAWINGS

An exemplary embodiment of the invention is illustrated in the drawing and is described in more detail hereinafter with reference thereto. In the figures.

DETAILED DESCRIPTION OF A PREFERRED EMBODIMENT

Figure 1:
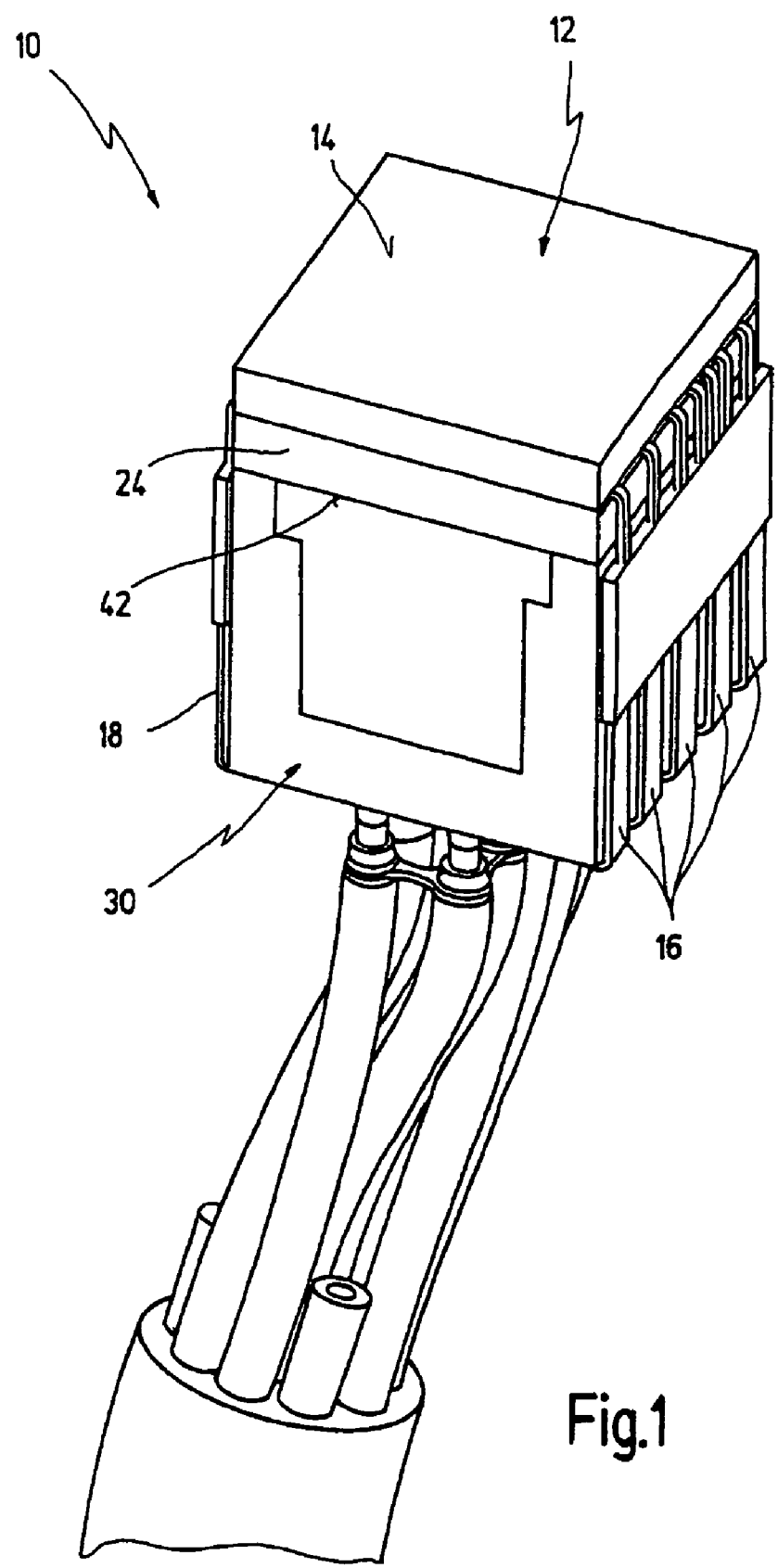
FIG. 1 shows a greatly enlarged illustration in a view obliquely from the distal end of an image pick-up module in the finished assembled state.
Figure 9:
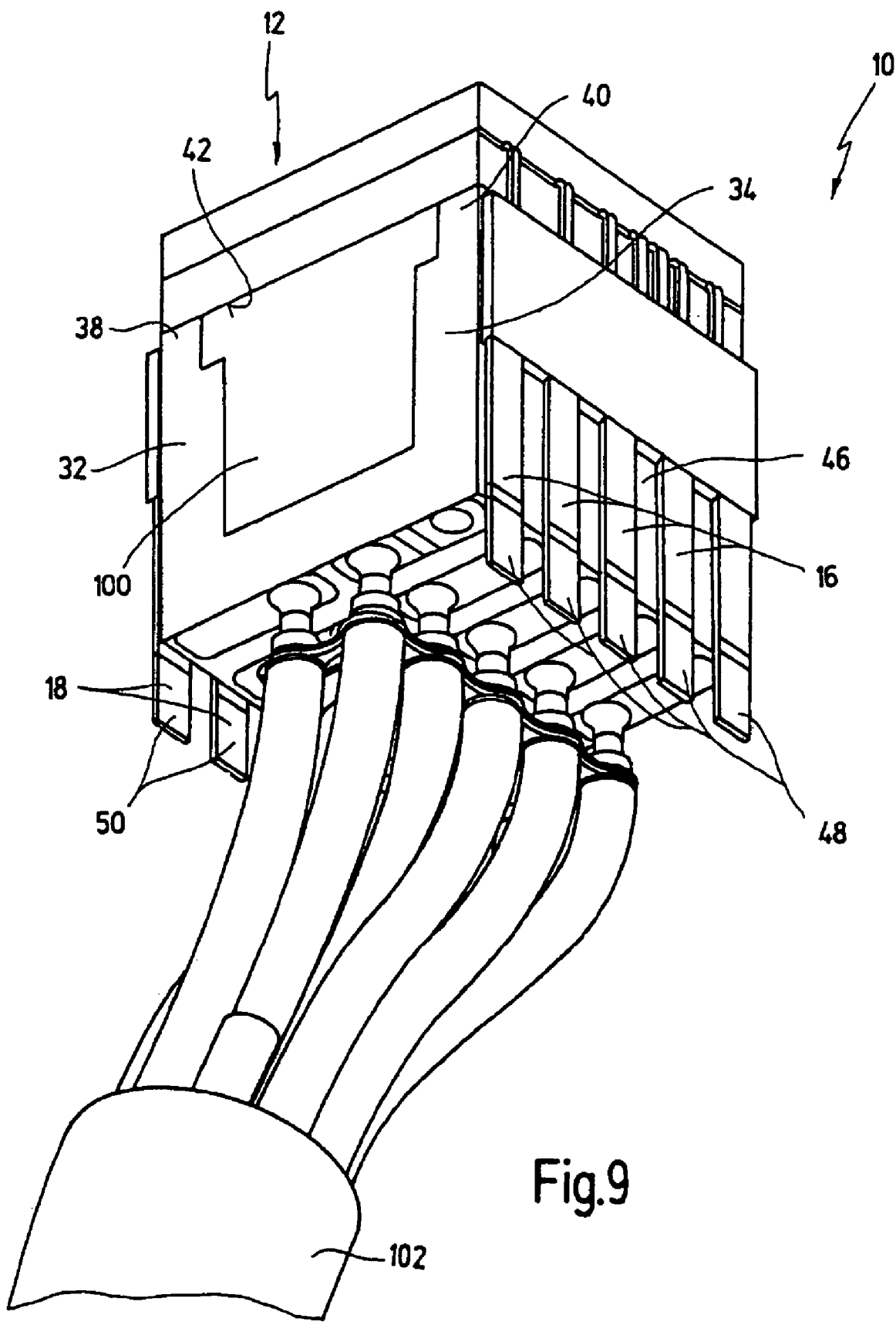
FIG. 9 shows yet another step of the method for assembly of the image pick-up module in FIG. 1 in a view obliquely from the proximal end.
Figure 10:
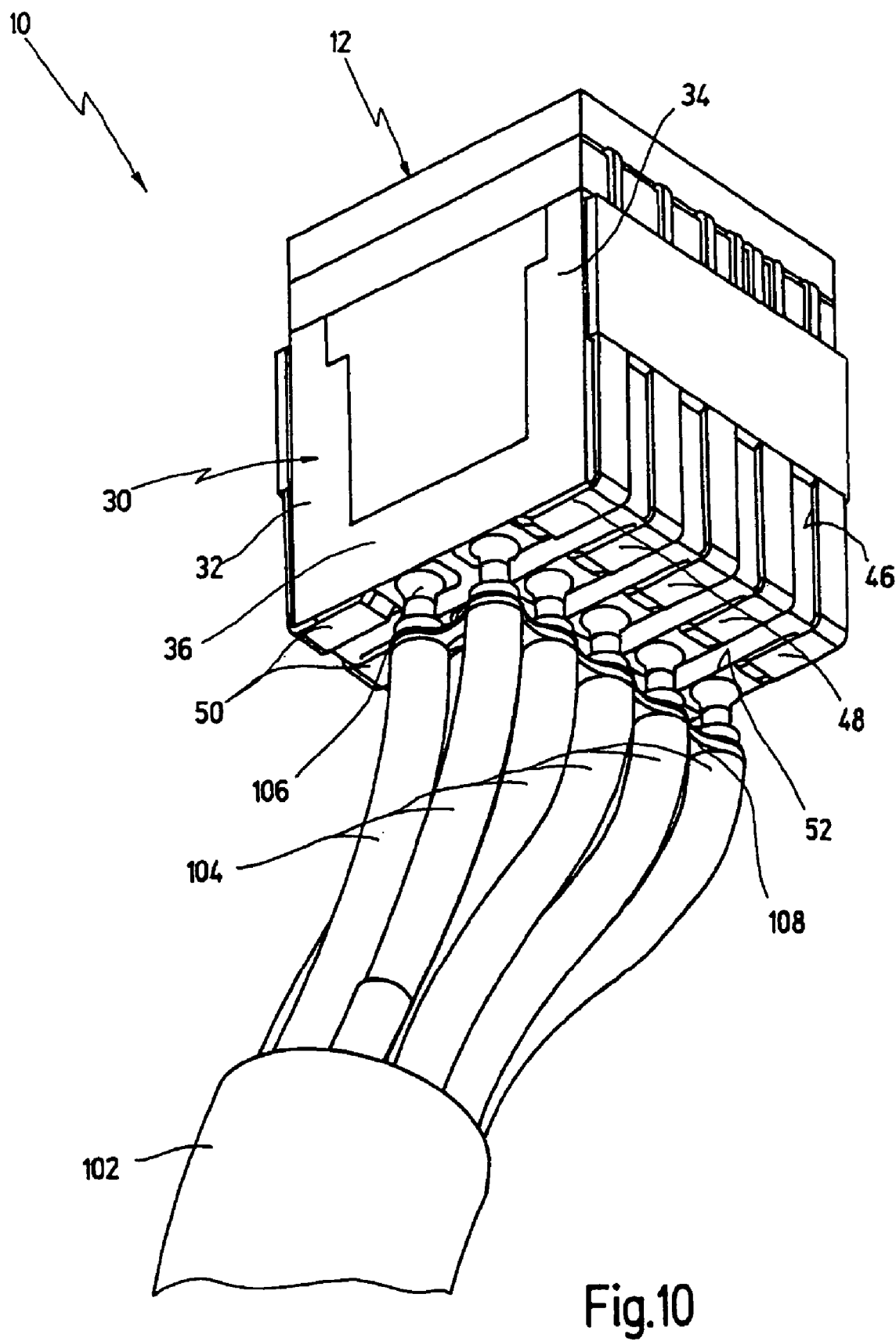
FIG. 10 shows the finished assembled image pick-up module after a last step of the method for assembly of the image pick-up module in a view obliquely from the proximal end.

FIGS. 1 and 10 illustrate an image pick-up module provided with the general reference symbol 10 in its entirety and in the finished assembled state. Details of the image pick-up module 10 are illustrated in FIGS. 2 to 9.

The image pick-up module 10 is preferably used in an endoscope (not illustrated), in particular a video endoscope, or in a miniaturized camera. The image pick-up module 10 is an optoelectronic component in miniaturized form. It goes without saying that the illustrations in FIGS. 1 to 10 are greatly enlarged.

The image pick-up module 10 has an electronic image sensor 12 as first main component. The image sensor 12 has an outer side 14 at the light entry end, through which light enters the image sensor 12. An imaging optical system is connected upstream of the outer side 14 at the light entry end when the image pick-up module 10 is in use, for example in the state in which it is installed in an endoscope, in the distal tip thereof, in order to image an object to be observed on the image sensor 12.

The image sensor 12 is embodied using CCD or CMOS technology in a TAB configuration.

Figure 3:
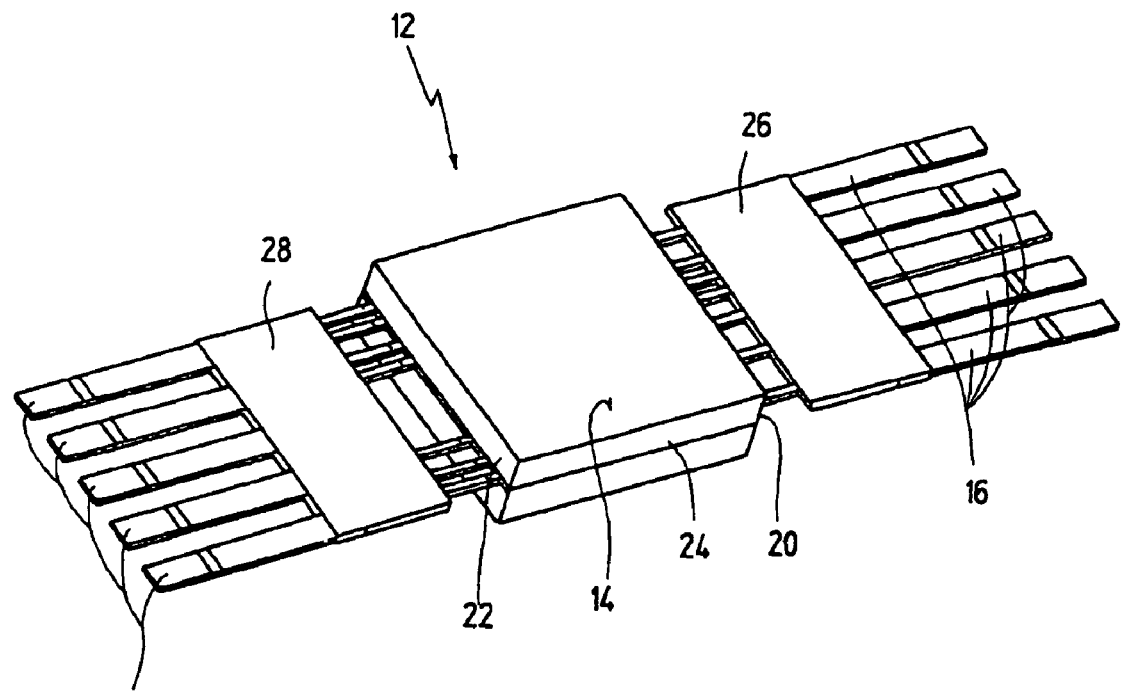
FIG. 3 shows an electronic image sensor of the image pick-up module in FIG. 1 in isolation in a view obliquely from the distal end.

The image sensor 12 has a plurality of contact fingers 16 and 18, a total of ten such contact fingers 16 and 18 in the present case. The contact fingers 16 and 18 are arranged in two rows on opposite sides 20 and 22 of a base body 24 of the image sensor 12. In this case, the contact fingers 16 form a first row of contact fingers and the contact fingers 18 form a second row of contact fingers. FIG. 3 illustrates the image sensor 12 in isolation in its initial state prior to assembly of the image pick-up module 10. In this initial state, the contact fingers 16 and 18 extend essentially parallel to the plane of the base part 24. The contact fingers 16 are connected to one another via a non-conductive lamina 26, and the contact fingers 18 correspondingly via a non-conductive lamina 28.

Figure 2:
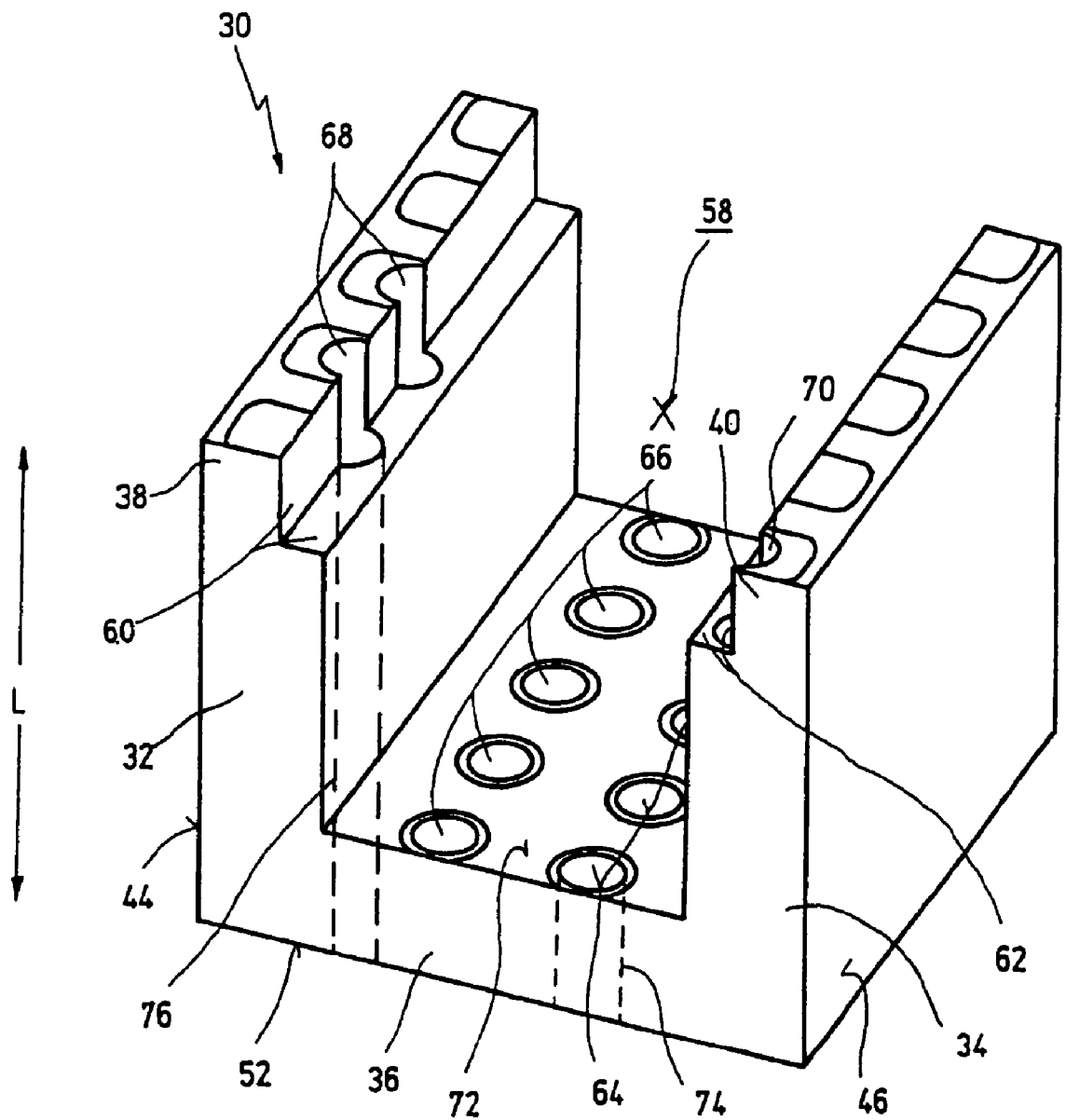
FIG. 2 shows a circuit board of the image pick-up module in FIG. 1 in isolation in a view obliquely from the distal end.

A further main component of the image pick-up module 10 is a circuit board 30 (FIG. 1), which is illustrated in isolation in FIG. 2.

The circuit board 30 has three sections 32, 34 and 36 that are connected to one another in one piece and in an unarticulated manner, the first section 32 and the second section 34 essentially running parallel and being spaced apart from one another and, in accordance with FIG. 1, extending essentially transversely with respect to the image sensor 12, while the third section 36 extends transversely with respect to the first section 32 and the second section 34 and essentially parallel to the image sensor 12. In accordance with FIG. 1, the image sensor 12 is arranged at ends 38 and 40 of the first and second sections 32 and 34 which are remote from the third section 36, and is fixed, for example adhesively bonded, hereon without any distance from the sections 32 and 34. An underside or inner side 42 remote from the outer side at the light entry end thus faces the circuit board 30.

The contact fingers 16 and 18 run along outer sides 44 and 46 of the first section 32 and second section 34, respectively.

The length L of the first section 32 and of the second section 34 is less than the length of the contact fingers 16 and 18, respectively, (cf. in particular FIG. 9), so that ends 48 and 50 of the contact fingers 16 and 18, respectively, engage around the sections 32 and 34, respectively, onto an outer side 52 of the third section 36, as is best illustrated in FIG. 10.

Figure 8:
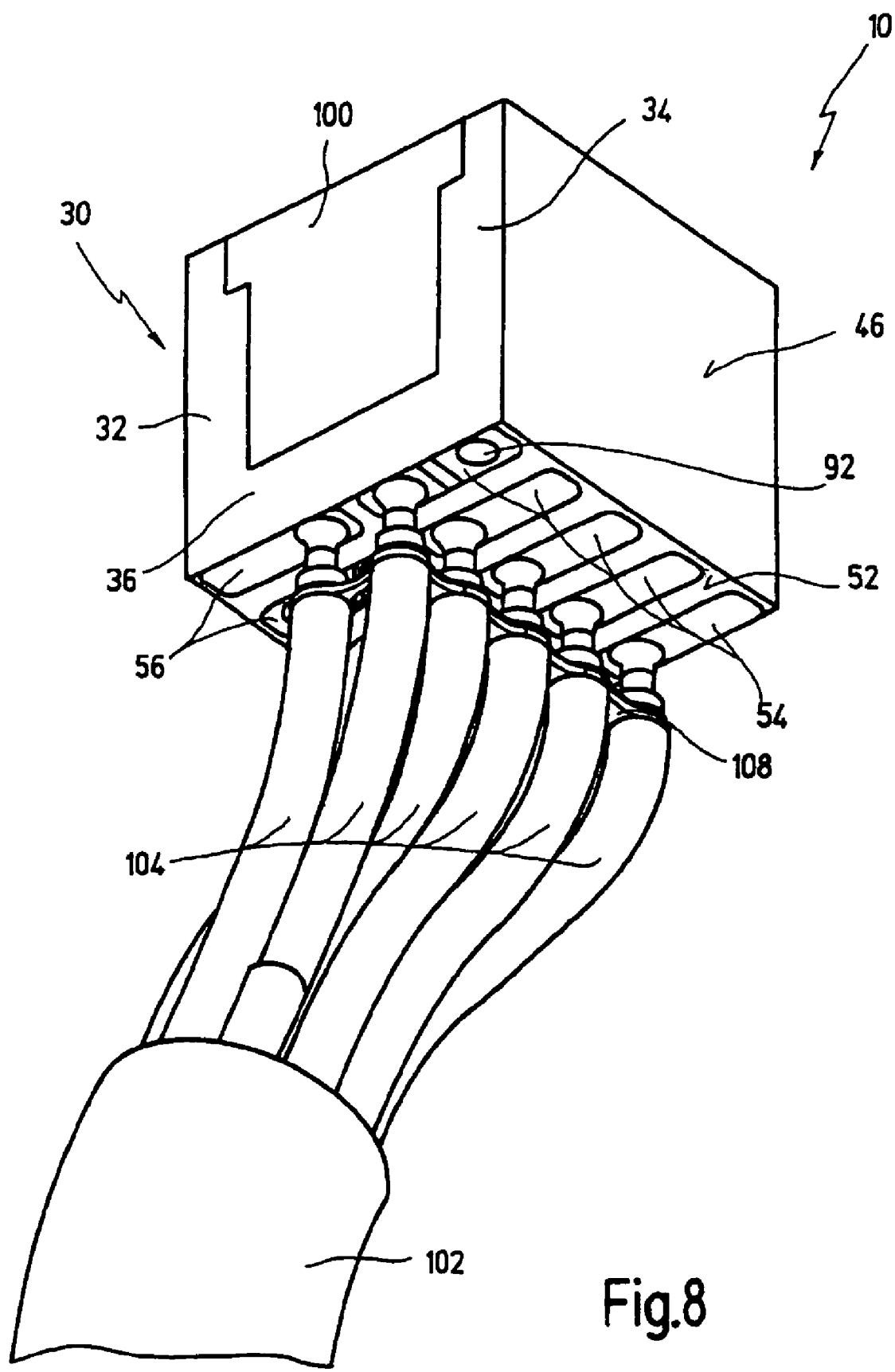
FIG. 8 shows yet another step of the method for assembly of the image pick-up module in a view obliquely from the proximal end.

At the outer side 52 of the third section 36, the contact fingers 16 and 18 are electrically contact-connected to the circuit board 30, which has corresponding contacts 54 and 56 at the outer side 52 of the third section (cf. FIG. 8).

With the exception of contact-connecting locations, for example the contacts 54 and 56, the circuit board 30 is produced altogether from a non-conductive material, for example from plastic.

Between the first section 32, the second section 34 and the third section 36, the circuit board 30 has a space 58 serving to receive electronic components, as will be described hereinafter.

During the production of the circuit board 30, the latter is originally produced from a parallelepipedal or cuboid bulk material into which a groove or notch is introduced by means of a material cutout from the bulk material, for example by milling out, in order to create the space 58. In this case, the groove or notch is open at three sides, as revealed in FIG. 2.

As revealed in FIG. 2, the space 58 between the sections 32, 34 and 36 has a T-shaped structure, the wider section being situated at the ends 38 and 40 of the sections 32 and 34 in the direction transversely with respect thereto. The space 58 thus has a step 60 at the first section 32 and a step 62 at the second section 34.

The circuit board 30 furthermore has a plurality of holes 64, 66, 68 and 70. The holes 64 and 66 extend through the third section 36 from the inner side 72 thereof as far as the outer side 52 thereof, as is indicated by interrupted lines 74 for one of the holes 64.

The holes 68 and 70 extend through the first section 32 and through the second section 34, respectively, and open in the region of the end 38 and 40, respectively, of the sections 32 and 34 at the steps 60 and 62, respectively, and at the opposite end likewise on the outer side 52 of the third section 36, as is indicated by interrupted lines 76 for one of the holes 68 in FIG. 2. All of the holes 64 to 70 are insulated from one another by the material of the circuit board 30. On the inner side, the holes 64 to 70 may be electrically conductively metallized, that is to say have a conductor, for example by the walls of the holes 64 to 70 being metallized, or the holes 64 to 70 being completely filled with a metal. In this way, the holes 64 to 70 constitute plated-through holes through the circuit board body 30.

Figure 4:
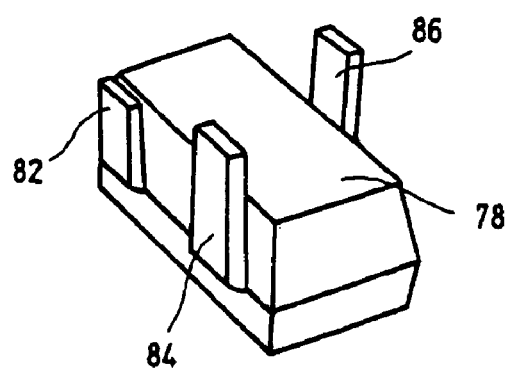
FIG. 4 shows an electronic component of the image pick-up module in FIG. 1 in isolation in a view obliquely from the distal end.
Figure 5:
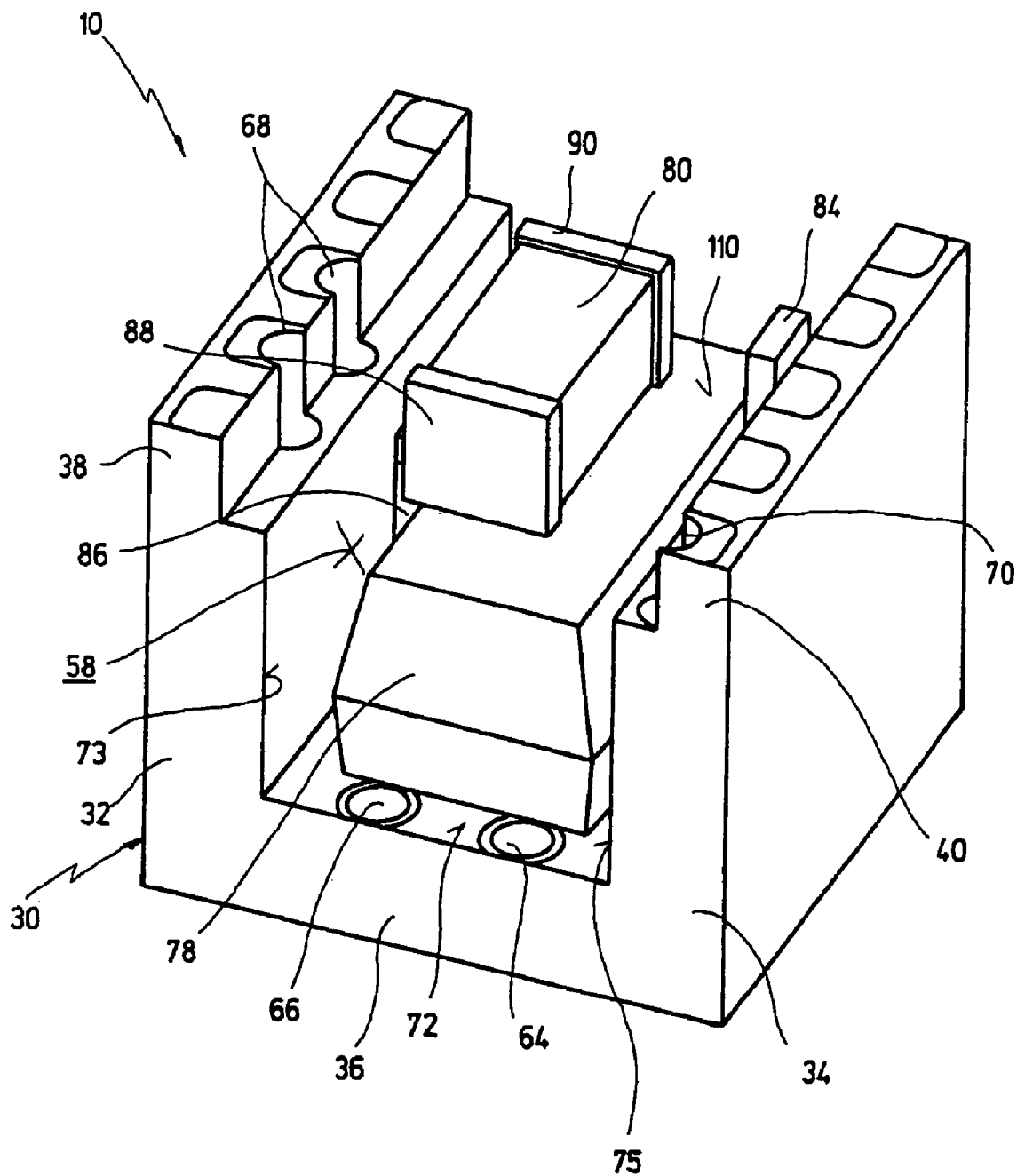
FIG. 5 shows a step of the method for assembly of the image pick-up module in FIG. 1 in a view obliquely from the distal end.

As is illustrated in FIG. 5, the space 58 between the first, second and third sections 32, 34, 36 serves to receive electronic components for the control electronics of the image sensor 12. In the present case, the image pick-up module 10 has a first electronic component 78 and a second electronic component 80. The first electronic component 78 is a transistor, illustrated in isolation in FIG. 4, and the second electronic component 80 is a capacitor. The first electronic component 78 is arranged on the inner side 72 of the third section 36 between the first and second sections 32 and 34 and fixed thereon, for example by adhesive bonding, and the second electronic component 80 is arranged on the first electronic component 78 and fixed thereon, likewise by means of adhesive bonding, by way of example. Consequently, the two electronic components 78 and 80 are arranged in a manner lying one above the other in the space 58, as a result of which the space 58 is optimally utilized in terms of its three-dimensional dimensions.

The first electronic component 78 has three contacts 82, 84, 86 (cf. FIG. 4) which project upwards from the electronic component 78, that is to say in a manner pointing towards the ends 38 and 40 of the sections 32 and 34, respectively. The transistor that forms the first electronic component 78 is, by way of example, a commercially available transistor in a miniaturized embodiment, the contacts 82, 84, 86, if appropriate prior to installation in the circuit board 30, as illustrated in FIG. 4, being bent and partly cut to length in order to achieve the suitable position and length for the contact-connection of the component 78.

The second electronic component 80 has two contacts 88 and 90 arranged at end sides of the component 80.

Figure 6:
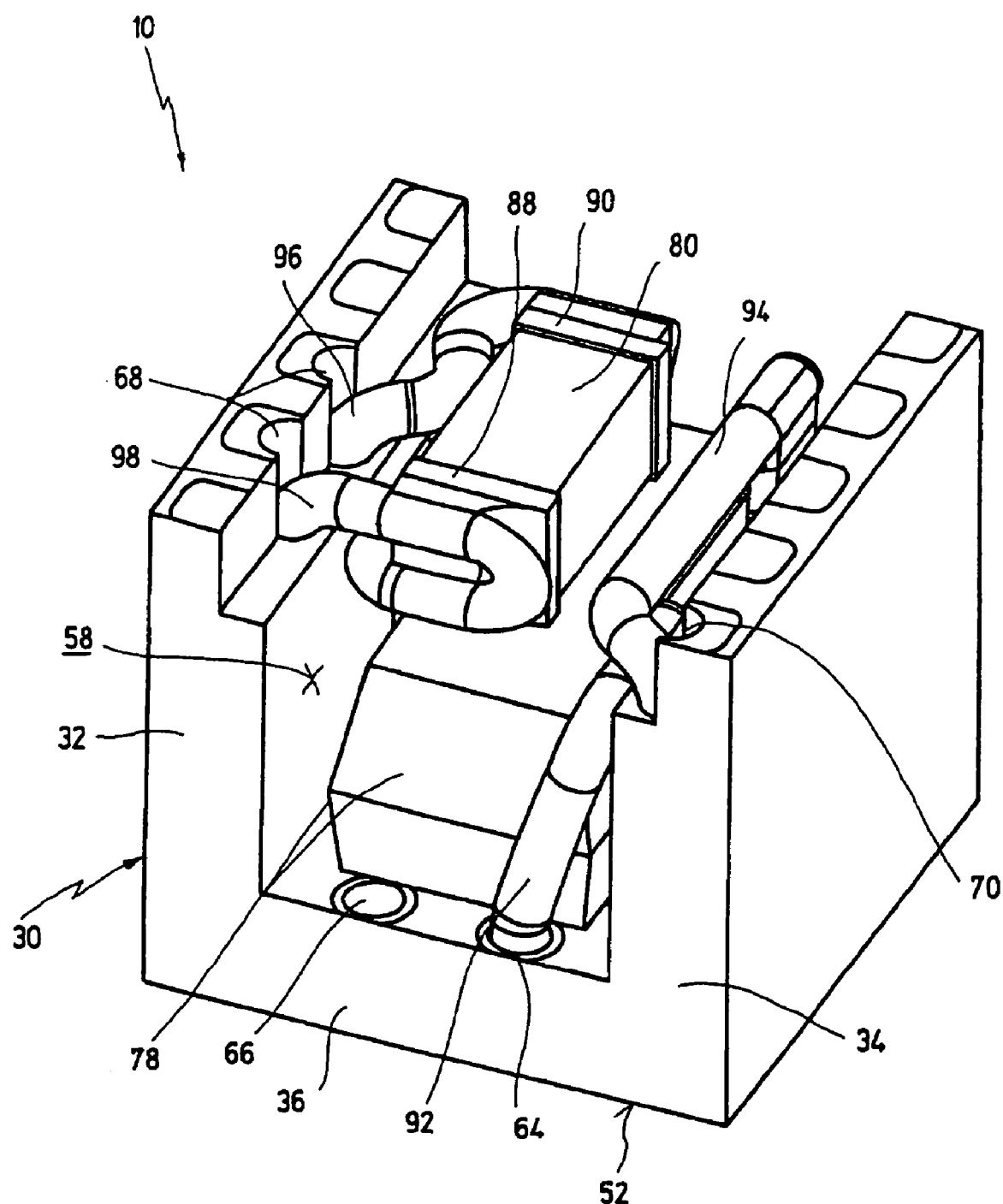
FIG. 6 shows a further step of the method for assembly of the image pick-up module in FIG. 1 in a view obliquely from the distal end.
Figure 7:
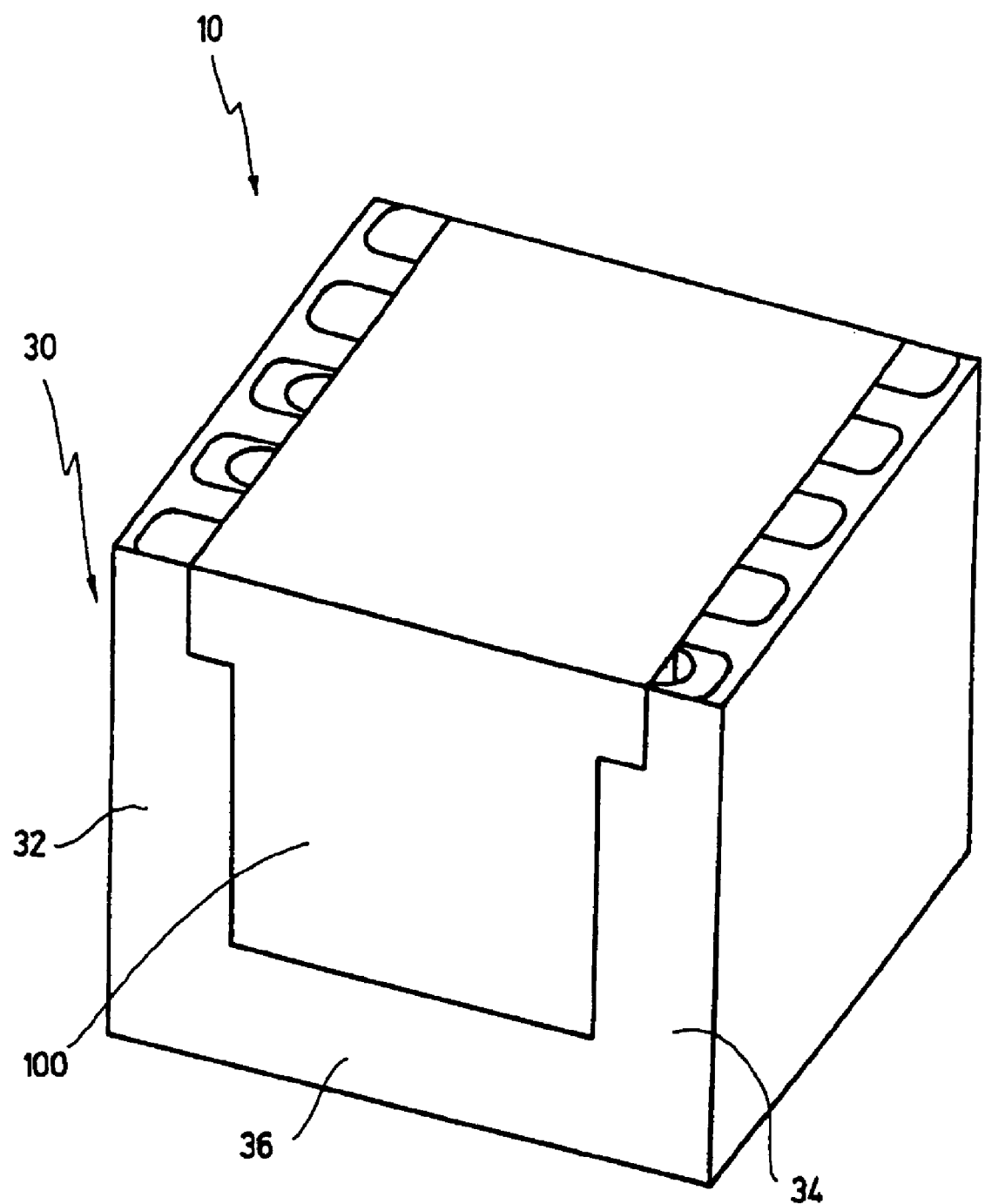
FIG. 7 shows yet another step of the method for assembly of the image pick-up module in FIG. 1 in a view obliquely from the distal end.

For electrically connecting, i.e. contact-connecting, the first and second electronic components 78 and 80 to the circuit board 30, in accordance with FIG. 6, a plurality of conductor wires 92 to 98 and a further conductor wire that cannot be seen in the drawing are provided. Five conductor wires 92 to 98 of this type are correspondingly provided in accordance with the number of, in total, five contacts of the electronic components 78 and 80. The conductor wires 92 to 98 are preferably formed without an insulating outer sheath in order to obviate the space requirement for such insulations. The conductor wires 92 to 98 are insulated in a different way that is described later.

At the electronic components 78 and 80, the individual conductor wires 92 to 98 are contact-connected thereto in each case at locations which are spaced apart from the first, second and third sections 32, 34, 36. In this way, the components 78 and 80 are also contact-connected in an optimally space-saving manner whilst utilizing the three-dimensionality of the space 58 in the circuit board 30.

The conductor wires 92 to 98 are led or at least through-plated through the holes 64 to 70 to the outer side 52 of the third section 36. Thus, by way of example, the conductor wire 92 is led or through-plated through the hole 64 in the third section 36 as far as the underside 52 of the third section 36, as can be seen in FIG. 8. The T-shaped configuration of the space 58 or of the groove 58 in this case has the advantage that, by way of example, the conductor wires 94, 96 and 98 can emerge from the corresponding holes 68 and 70 without the risk of coming into contact with the image sensor 12 situated thereabove or impeding the later fitting of the image sensor 12 on the sections 32 and 34.

The actual contact-connection of the components 78 and 80 is effected on the basis of the leadthrough or through-plating of the conductor wires 92 to 98 on the outer side 52 of the third section 36 of the circuit board 30, as has already been explained above for the conductor wire 92 with reference to FIG. 8.

The rest of the remaining region of the space 58 between the sections 32, 34 and 36 of the circuit board 30 and the components 78 and 80 is filled with a curing filling composition 100, the filling composition 100 being, by way of example, an epoxy resin that is initially present in liquid form and has a sufficient low viscosity in the liquid state to pass into all of the remaining free interspaces and partial regions of the space 58. In this case, the filling composition 100 simultaneously brings about an insulation of the conductor wires 92 to 98 and of all the electrically conductive surfaces, for example of the contacts 82 to 86 of the first component 78 and the contacts 88 and 90 of the second component 80. In FIGS. 1, 7 to 10, the filling composition 100 is illustrated as non-transparent, with the result that the components 78 and 80 situated in the space 58, the conductor wires 92 to 98 and the inner sides 72, 73 and 75 of the sections 32, 34, 36 cannot be seen in these illustrations.

However, the filling composition 100 may equally also be formed in transparent fashion.

In accordance with FIGS. 1, 8, 9 and 10, the image pick-up module 10 is connected to a cable 102 having a plurality of cores 104. The cores 104 are in each case individually contact-connected to the circuit board 30, 106 designating a contact-connecting location for one of the cores 104 in FIG. 10. In this case, the cores 104 are contact-connected at the underside 52 of the third section 36 of the circuit board 30, in the same way as the ends 48 and 50 of the contact fingers 16 and 18, respectively, of the image sensor 12.

A shielding element 108 embodied in the form of a plate is connected to the individual cores 104 for the purpose of electrical shielding.

The cable 102 or the cores 104 are preferably releasably connected to the circuit board 30. This may be effected, in a manner that is not illustrated, by provision of a further circuit board embodied complementarily to the outer side 52 of the third section 36 of the circuit board 30. The individual cores are then contact-connected to the said additional circuit board, and the circuit board as a whole is connected to the outer side 52 of the third section 36 of the circuit board 30, for example by soldering. If the image pick-up module 10 is then to be disconnected from the cable 102, only the soldering location or adhesive-bonding location between the additional circuit board and the circuit board 30 has to be released, which is simpler than having to unsolder each individual core 104 from the outer side 52 of the third section 36 of the circuit board 30.

The image pick-up module 10 has a cuboid structure overall, the side dimensions of the cuboid structure being approximately 2 mm×2 mm or smaller. The outer sides 44 and 46 of the first section 32 and of the second section 34 of the circuit board 30 may also taper towards the proximal end as seen from the image sensor 12, that is to say be inclined towards the centre of the third section 36. However, it is also possible for the sections 32 and 34 as a whole to be inclined towards the centre of the third section 36.

Furthermore, channel-like depressions may be provided on the outer sides 44 and 46 of the first section 32 and of the second section 34 of the circuit board 30 in order to receive the contact fingers 16 and 18 therein, so that the contact fingers 16 and 18 of the image sensor 12 are not applied on the outer sides 44 and 46 of the sections 32 and 34 of the circuit board 30.

Furthermore, it might be provided that the contact fingers 16 and 18 of the image sensor 12 are in part also contact-connected to the circuit board 30 on the outer side at the sections 32 and 34, so that there is more space for contact-connecting the cable 102 or the cores 104 thereof on the underside 52 of the third section 36 of the circuit board 30.

A method for assembly of the image pick-up module 10 will be described below.

Firstly, the circuit board 30 in accordance with FIG. 2 and the image sensor 12 in accordance with FIG. 3 are provided.

The circuit board 30 in accordance with FIG. 2 may be produced beforehand from a cuboid or parallelepipedal piece of bulk material by means of a material cutout in order to produce the space 58 between the first section 32, the second section 34 and the third section 36. Furthermore, the holes 64, 66, 68, 70 are introduced into the circuit board 30; if appropriate, these holes are provided with metallizations as described above.

In the next step, firstly the first electronic component 78 is provided, if appropriate the contacts 82 to 86 of the component 78 being bent into the correct position in accordance with FIG. 4 and, if appropriate, cut to length.

Afterwards, in accordance with FIG. 5, the first electronic component 78 is positioned on the inner side 72 of the third section 36 and fixed there, for example by being adhesively bonded. The second electronic component 80 is positioned on a side 110, that is to say on the electronic component 78, and fixed thereto, for example by adhesive bonding.

In the next step, the conductor wires 92 to 98, which have previously been bent into the form introduced in FIG. 6, are electrically conductively connected, i.e. contact-connected (FIG. 6), to the contacts 82 to 86 of the first component 78 and/or 88 and 90 of the second component 80. Moreover, the conductor wires 92 to 98 are through-plated through the holes 64, 66, 68 and 70 to the outer side 52 of the third section 36.

After the electronic components 78 and 80 have been contact-connected to the circuit board 30, the remaining part of the space 58 of the circuit board 30 is filled with the filling composition 100 and the filling composition 100 is subsequently cured.

In the next step, in accordance with FIG. 8, the cable 102 with the cores 104 is contact-connected at the underside 52 of the third section 36. The cores 104, in accordance with FIG. 8, have previously been exposed and provided with the shielding element. The free ends of the cores 104 have likewise previously been stripped of insulation. The cores are contact-connected to the underside 52 of the third section 36 of the circuit board 30 by means of a customary contact-connecting technique, such as soldering, for example.

After the contact-connection of the cable 102 at the circuit board 30, the image sensor 12 is placed directly by its underside 42 onto the ends 38 and 40 of the sections 32 and 34 of the circuit board 30 and the cured filling composition 100, i.e. without any distance from the ends 38 and 40. The contact fingers 16 and 18 of the image sensor 12 are bent over approximately at right angles to the plane of the image sensor 12 and arranged along the outer sides 44 and 46 of the sections 32 and 34. (FIG. 9).

Finally, in the last step, the ends 48 and 50 of the contact fingers 16 and 18, respectively, of the image sensor 12 are bent over onto the outer side 52 of the third section 36 of the circuit board 30, as is illustrated in FIG. 10, the ends 48 and 50 then being contact-connected to the circuit board 30. The image sensor 12, the electronic components 78, 80 and the cable 102 are now all contact-connected on the outer side 52 of the third section 36 of the circuit board 30 and electrically interconnected in accordance with the predetermined terminal allocation plan.

The order to contact-connecting the cable 102 and fitting the image sensor to the circuit board 30 is preferably also possible in the opposite order, that is to say that firstly the image sensor 12 is fixed to the circuit board 30 and the contact fingers 16 and 18 are contact-connected to the circuit board, and only afterwards is the cable 102 then contact-connected to the circuit board 30.

What is claimed is:

1. An image pick-up module, comprising:
   an electronic image sensor having a body and a plurality of contact fingers arranged in two rows on opposite sides of said body and each having a length,
   a rigid circuit board to which said contact fingers are electrically contact-connected,
   said circuit board having at least three sections connected to one another in one piece, a first and a second section of said at least three sections extending in a manner spaced apart from one another essentially transverse with respect to said image sensor, and a third section of said at least three sections extending essentially parallel to said image sensor, said first, second and third sections being connected to one another in an unarticulated manner, said image sensor being arranged at an end of said first and second sections which is remote from said third section,
   at least one of said two rows of said contact fingers of said image sensor running along an outer side of at least one of said first and second sections, a length of at least one of said first and second sections being not larger than said length of at least a portion of said contact fingers, and
      at least one electronic component of control electronics for said image sensor, said at least one electronic component being arranged in a space configured as a notch or a groove present between said first, second and third sections of said circuit board.

2. The image pick-up module of claim 1, wherein said contact fingers of said image sensor that run along said at least one of said first and second sections at least partly engage on an outer side of said third section of said circuit board and are contact-connected to said circuit board at said outer side of said third section.

3. The image pick-up module of claim 1, wherein both of said two rows of said contact fingers are led past said outer side of said first section and said second section and are contact-connected to said circuit board on an outer side of said third section of said circuit board.

4. The image pick-up module of claim 1, wherein depressions for receiving said contact fingers are formed on said outer side of at least one of said first and second sections.

5. The image pick-up module of claim 1, wherein at least two electronic components are arranged in said space between said first, second and third sections of said circuit board in a manner lying one above the other in a direction from said third section to said image sensor.

6. The image pick-up module of claim 1, wherein said at least one electronic component is contact-connected to at least one conductor wire at a location of said space which is at a distance from said first, second and third sections.

7. The image pick-up module of claim 6, wherein said at least one conductor wire, proceeding from said at least one electronic component, is at least partly led through a hole that extends through at least one of said first, second or third section and opens at an outer side of said third section.

8. The image pick-up module of claim 1, wherein a remaining free part of said space between said first, second and third sections and said at least one electronic component is filled with an insulating curable filling composition.

9. The image pick-up module of claim 1, wherein said circuit board is produced from a parallelepipedal bulk material, and said space between said first, second and third sections is formed by a material cutout from said bulk material.

10. The image pick-up module of claim 1, wherein said space between said first, second and third sections has approximately the form of a T in cross section, a wider section of said space being situated at said ends of said first and second sections which face said image sensor.

11. The image pick-up module of claim 1, wherein said image sensor is fixed directly to said ends of said first and second sections of said circuit board which are remote from said third section.

12. The image pick-up module of claim 1, wherein a plurality of holes extend through at least one of said first and second sections of said circuit board, which holes proceed from an outer side of said third section and open at an inner side of at least one of said first section, said second section, and said third section.

13. The image pick-up module of claim 1, wherein at least of said first and second sections, at least on an outer side, run obliquely with respect to a centre axis of said third section towards said third section.

14. The image pick-up module of claim 1, wherein said image pick-up module is formed in approximately cuboid fashion and has side dimensions of approximately 2 mm ×2 mm to the maximum.

15. The image pick-up module of claim 1, wherein said circuit board is connected to a multi-core cable, and said cable is contact-connected to said circuit board at an outer side of said third section.

16. The image pick-up module of claim 15, wherein said cable is releasably connected to said circuit board.

17. The image pick-up module of claim 1, wherein at least one of said two rows of said contact fingers is cut to length and contact-connected to said circuit board on said outer side of at least one of said first and second sections.

18. A method for assembly of an image pick-up module, comprising:
   providing an electronic image sensor having a body and a plurality of contact fingers arranged in two rows on opposite sides of said body and each having a length,
   providing a rigid circuit board having at least three sections, a first and a second section of said at least three sections extending in a manner spaced apart from one another essentially in a first direction, and a third section of said at least three sections extending in a second direction essentially transversely with respect to said first direction, wherein said circuit board is provided with a length which is not larger than said length of said contact fingers and providing said circuit board with a space configured as a notch or a groove between said first, second and third sections, fitting said imagine sensor to an end of said first and second sections which is remote from said third section, arranging said contact fingers of at least one of said two rows along an outer side of at least one of said first and second sections and electrically contact-connecting said contact fingers to said circuit board, and inserting at least one electronic component in said space and contact-connecting said electronic component to said circuit board before fitting said image sensor to said circuit board.

19. The method of claim 18, further comprising, prior to providing said circuit board, producing said circuit board from a parallelepipedal bulk material, and introducing a groove into said bulk material by means of a material cutout, thereby forming said first, second and third sections of said circuit board and said space between said first, second and third sections.

20. The method of claim 18, further comprising, prior to fitting said image sensor to said circuit board, inserting at least two electronic components into said space between said first, second and third sections, and contact-connecting said at least two electronic components to said circuit board, and fitting said at least two electronic components on said third section in an arrangement lying one above the other.

21. The method of claim 18, further comprising contact-connecting said at least one electronic component to at least one conductor wire at a location of said space between said first, second and third sections.

22. The method of claim 18, further comprising contact-connecting said at least one component at an outer side of said third section.

23. The method of claim 18, further comprising filling said free space between said first, second and third sections which remains after said inserting of said at least one electronic component with a curing filling composition.

24. The method of claim 23, further comprising filling said filling composition into said space prior to fitting said image sensor to said circuit board.

25. The method of claim 18, further comprising diverting said contact fingers of at least one of said two rows of said image sensor onto an outer side of said third section and contact-connecting said contact fingers to said circuit board on said outer side.

26. The method of claim 18, further comprising contact-connecting a multicore cable to said circuit board at an outer side of said third section.

\* \* \* \* \*